United States Patent
Takahashi

(10) Patent No.: US 11,112,595 B2
(45) Date of Patent: Sep. 7, 2021

(54) ENDOSCOPE AND ADAPTOR FOR ENDOSCOPE

(71) Applicant: OLYMPUS CORPORATION, Tokyo (JP)

(72) Inventor: Susumu Takahashi, Iruma (JP)

(73) Assignee: OLYMPUS CORPORATION, Tokyo (JP)

(*) Notice: Subject to any disclaimer, the term of this patent is extended or adjusted under 35 U.S.C. 154(b) by 761 days.

(21) Appl. No.: 15/684,171

(22) Filed: Aug. 23, 2017

(65) Prior Publication Data

US 2017/0351086 A1 Dec. 7, 2017

Related U.S. Application Data

(63) Continuation of application No. PCT/JP2016/084633, filed on Nov. 22, 2016.

(30) Foreign Application Priority Data

Dec. 25, 2015 (JP) .............................. JP2015-254254

(51) Int. Cl.
*A61B 1/00* (2006.01)
*G02B 23/26* (2006.01)
*G02B 23/24* (2006.01)
*G02B 27/10* (2006.01)
(Continued)

(52) U.S. Cl.
CPC .......... *G02B 23/26* (2013.01); *A61B 1/00013* (2013.01); *A61B 1/00096* (2013.01);
(Continued)

(58) Field of Classification Search
CPC ................ G02B 23/2476; G02B 23/24; G02B 23/2407; G02B 23/2415; G02B 23/2423;
(Continued)

(56) References Cited

U.S. PATENT DOCUMENTS 5,940,126 A * 8/1999 Kimura ................ H04N 5/2253
348/294
6,154,315 A * 11/2000 Street ................. A61B 1/00193
348/45
(Continued)

FOREIGN PATENT DOCUMENTS

JP 7-311348 A 11/1995
JP 9-248276 A 9/1997
(Continued)

OTHER PUBLICATIONS

International Search Report dated Feb. 14, 2017 received in PCT/JP2016/084633.

*Primary Examiner* — Ryan N Henderson
*Assistant Examiner* — Pamela F Wu
(74) *Attorney, Agent, or Firm* — Scully, Scott, Murphy & Presser, P.C.

(57) ABSTRACT

An adaptor including: first and second optical systems; a prism comprising a mirror region, first light flux and second light flux from the respective optical systems, being incident on the prism, the light flux passing through the prism at a portion, the second light flux being reflected by a mirror region after passing through the portion, the light flux emitted from the prism to a region; and a light-shield at the region, the light-shield shields one of the first and second light flux and is disposed proximally to the prism relative to an imaging system of the endoscope when the adaptor is attached to an endoscope; the first optical system is disposed such that the first light flux is incident in a direction parallel to an optical axis, the second optical system is disposed so that the second light flux is incident in a direction orthogonal to the optical axis.

14 Claims, 8 Drawing Sheets

(51) Int. Cl.
*A61B 1/06* (2006.01)
*A61B 1/05* (2006.01)

(52) U.S. Cl.
CPC ...... *A61B 1/00101* (2013.01); *A61B 1/00177* (2013.01); *A61B 1/00181* (2013.01); *A61B 1/0676* (2013.01); *G02B 23/243* (2013.01); *G02B 23/2453* (2013.01); *G02B 27/10* (2013.01); *A61B 1/05* (2013.01)

(58) Field of Classification Search
CPC .............. G02B 23/243; G02B 23/2438; G02B 23/2446; G02B 23/2453; G02B 27/10; G02B 27/106; G02B 27/1066; G02B 27/126; G02B 23/02; G02B 23/04; G02B 26/06; G02B 26/08; G02B 23/26; G02B 27/14; G02B 27/141; G02B 27/144; A61B 1/00013; A61B 1/00096; A61B 1/0008; A61B 1/00101; A61B 1/00177; A61B 1/00174; A61B 1/00179; A61B 1/00181; A61B 1/00183; A61B 1/04; A61B 1/00186; A61B 1/0676
USPC ................ 600/173, 109, 111–112, 129, 160, 600/164–168, 170–172, 175–176, 174
See application file for complete search history.

(56) References Cited

U.S. PATENT DOCUMENTS

| | | | |
|---|---|---|---|
| 6,306,082 | B1 | 10/2001 | Takahashi et al. |
| 6,361,491 | B1* | 3/2002 | Hasegawa .......... A61B 1/00096 348/45 |
| 2010/0195007 | A1* | 8/2010 | Takahashi .............. G02B 13/06 349/16 |
| 2012/0127567 | A1* | 5/2012 | Schouwink .......... G02B 23/243 359/372 |
| 2012/0253121 | A1* | 10/2012 | Kitano ................. A61B 1/0623 600/109 |
| 2015/0080654 | A1* | 3/2015 | Kuhn ..................... A61B 1/051 600/111 |

FOREIGN PATENT DOCUMENTS

| | | |
|---|---|---|
| JP | 2001-299679 A | 10/2001 |
| JP | 2003-164418 A | 6/2003 |
| JP | 2005-261557 A | 9/2005 |
| JP | 2009-506 A | 1/2009 |
| JP | 2010-128354 A | 6/2010 |
| JP | 2012-526293 A | 10/2012 |
| WO | 2010/127827 A1 | 11/2010 |

* cited by examiner

ENDOSCOPE AND ADAPTOR FOR ENDOSCOPE

CROSS-REFERENCE TO RELATED APPLICATIONS

This application is a continuation application of PCT/JP2016/084633, filed on Nov., 22 2016 which is based on and claims the benefit of priority from JP 2015-254254, filed on Dec. 25, 2015, the entire contents of each of which is incorporated herein by reference.

FIELD

The present application relates to endoscopes and adaptors for endoscopes, and more particularly relates to an endoscope and an adaptor for endoscope enabling observation in a plurality of directions.

PRIOR ART

Conventionally endoscopes have been widely used in the medical and industrial fields. Endoscopes include forward-viewing endoscopes and side-viewing endoscopes as well as endoscopes for stereo measurement.

This stereo-measurement endoscope is used to measure the size and the depth of a subject by taking an image of the subject at a part to be observed from two directions, calculating the displacement of measurement points between the obtained two images by correlation operation, and obtaining the size and the depth of the subject from the calculated displacement based on the principle of triangulation. In that case, two objective lenses are disposed at the leading end of the inserted portion of the endoscope to have two optical paths having a parallax.

In conventional stereo-measurement endoscopes, two left and right images having a parallax are projected on different regions on the imaging area of one imaging device. In order to obtain a more precise image, it is known for an endoscope to be configured to switch left and right images in a time-division manner and project them on a common region on the imaging area of one image pickup device.

For examination of a tubular path, such as a pipe, in a short time, it is known for an endoscope device to include an optical adaptor enabling observation in two directions including the forward-viewing and the side-viewing. To enable such an observation in two directions, two objective lenses are disposed at the optical adaptor, which include an objective lens for forward-viewing and an objective lens for side-viewing.

However, if an endoscope capable of obtaining two images viewed from different directions and not a stereo-measurement endoscope is configured to project a light flux of two optical paths on common region of one image pickup device to achieve a more precise image, the outer diameter of each objective optical system will increase. This results in a problem that the outer diameter of the optical adaptor and the leading end of the inserted portion of the endoscope increase.

For instance, the above-stated endoscope capable of observing in two directions of the forward-viewing and the side-viewing is configured to switch two images and project the images on a common region on the imaging area of one image pickup device. Then, the light flux in each direction from the front and the side will be thick in cross section, and so the outer diameter of the lens at each observation window has to increase and these two lenses at the observation windows have to be separated in position. This leads to the problem that the outer diameters of the optical adaptor and of the leading end of the inserted portion of the endoscope increase.

SUMMARY

Accordingly, an endoscope is provided. The endoscope comprising: a first optical system, a first light flux from a first region of a subject being incident on the first optical system; a second optical system, a second light flux from a second region of the subject being incident on the second optical system, the second light flux being in a direction orthogonal to the first light flux, the second region being different from the first region; a prism comprising a mirror region, the first light flux and the second light flux each being incident on the prism, the first light flux and the second light flux passing through the prism at an intersecting portion of the prism, the second light flux being reflected by the mirror region after passing through the intersecting portion, the first light flux and the second light flux being emitted from the prism to a predetermined region; a light-shield disposed at the predetermined region, the light-shield being configured to selectively shield one of the first light flux and the second light flux; an image sensor comprising an imaging area; and an imaging optical system disposed closer to the image sensor than the light-shield is, the imaging optical system being configured to form images of the first light flux passing through the first optical system and of the second light flux passing through the second optical system at a common region of the imaging area; wherein the first optical system is disposed such that the first light flux is incident in a direction substantially parallel to an optical axis of the imaging optical system; and the second optical system is disposed so that the second light flux is incident in a direction substantially orthogonal to the optical axis of the imaging optical system.

The endoscope can further comprise: a first deflecting optical system configured to deflect the first light flux emitted from the prism; and a second deflecting optical system configured to deflect the second light flux emitted from the prism; wherein the first light flux and the second light flux pass through the first deflecting optical system and the second deflecting optical system, respectively, and then are incident on the imaging optical system. The first deflecting optical system and the second deflecting optical system can be decentered lenses. Each of the first deflecting optical system and the second deflecting optical system can include a prism.

The light-shield can include a diaphragm movable between a first position to shield the first light flux and a second position to shield the second light flux.

The prism can be disposed such that the first light flux is emitted toward a region of the prism other than the mirror region; and the second incident optical system can be disposed such that the second incident light is emitted toward the mirror region.

The first optical system can be disposed such that the first light flux is incident in a direction parallel to the optical axis of the imaging optical system; and the mirror region can be disposed in a region of the prism such that the first light flux is not incident on the mirror region.

The prism can comprise a cuboid portion and a quadrangular-prism shaped portion, the quadrangular-prism shaped portion can have an end surface obliquely formed at a predetermined angle; the mirror region can be disposed on the end surface; the first light flux can pass through the cuboid portion and be emitted to the predetermined region; the second light flux can pass through the cuboid portion, is subsequently incident on the end surface, reflected by the mirror region and emitted to the predetermined region. The prism can comprise a cuboid portion and a quadrangular-prism shaped portion, the quadrangular-prism shaped portion can have an end surface obliquely formed at a predetermined angle; the mirror region can be disposed on the end surface; the first light flux can pass through the cuboid portion and the quadrangular-prism shaped portion and be emitted to the predetermined region; the second light flux can be incident on the quadrangular-prism shaped portion, incident on the end surface, reflected by the mirror region and emitted to the predetermined region.

The first optical system can be disposed such that the first light flux is incident in a direction parallel to the optical axis of the imaging optical system; and the mirror region can be disposed in a region of the prism such that the first light flux is not incident on the mirror region.

Also provided is an adaptor for attachment to an insertion portion of an endoscope. The adaptor comprising: a first optical system, a first light flux from a first region of a subject being incident on the first optical system; a second incident optical system, a second light flux from a second region of the subject being incident on the second optical system, the second light flux being in a direction orthogonal to the first light flux, the second region being different from the first region; a prism comprising a mirror region, the first light flux and the second light flux each being incident on the prism, the first light flux and the second light flux passing through the prism at an intersecting portion of the prism, the second light flux being reflected by the mirror region after passing through the intersecting portion, the first light flux and the second light flux being emitted from the prism to a predetermined region; and a light-shield disposed at the predetermined region, the light-shield being configured to selectively shield one of the first light flux and the second light flux; wherein the light shield is disposed more proximally than the prism relative to an imaging optical system disposed at a distal end of the insertion portion of the endoscope when the adaptor is attached to the insertion portion; the first optical system is disposed such that the first light flux is incident in a direction substantially parallel to an optical axis of the imaging optical system; and the second optical system is disposed so that the second light flux is incident in a direction substantially orthogonal to the optical axis of the imaging optical system.

The prism can be disposed such that the first light flux is emitted toward a region of the prism other than the mirror region; and the second incident optical system can be disposed such that the second incident light is emitted toward the mirror region.

The prism can comprise a cuboid portion and a quadrangular-prism shaped portion, the quadrangular-prism shaped portion can have an end surface obliquely formed at a predetermined angle; the mirror region can be disposed on the end surface; the first light flux can pass through the cuboid portion and be emitted to the predetermined region; the second light flux can pass through the cuboid portion, is subsequently incident on the end surface, reflected by the mirror region and emitted to the predetermined region.

The prism can comprise a cuboid portion and a quadrangular-prism shaped portion, the quadrangular-prism shaped portion can have an end surface obliquely formed at a predetermined angle; the mirror region can be disposed on the end surface; the first light flux can pass through the cuboid portion and the quadrangular-prism shaped portion and be emitted to the predetermined region; the second light flux can be incident on the quadrangular-prism shaped portion, incident on the end surface, reflected by the mirror region and emitted to the predetermined region.

DETAILED DESCRIPTION

The following describes the embodiments with reference to the drawings.

Figure 1:
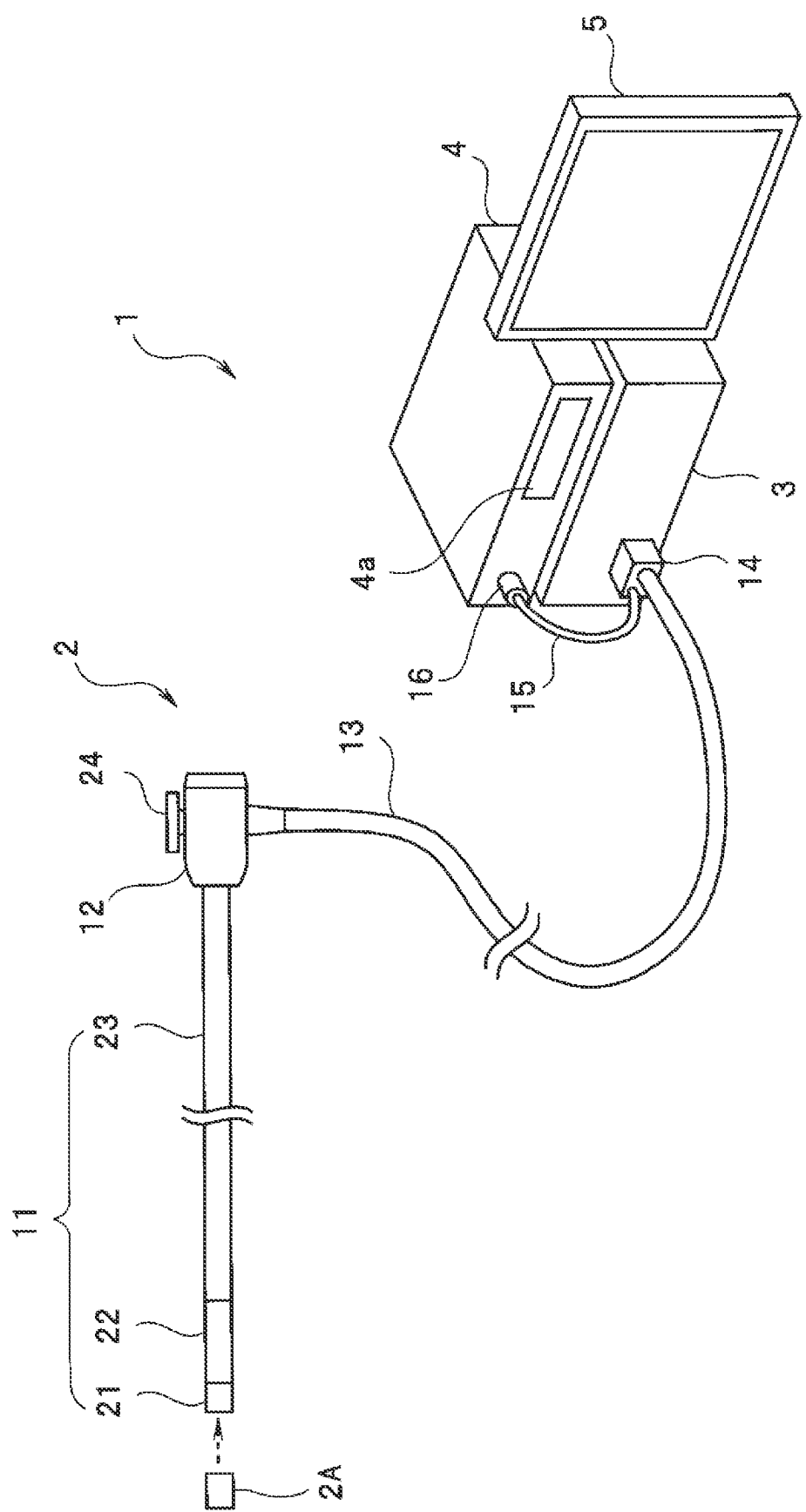
FIG. 1 shows the configuration of an endoscopic device according to one embodiment.

FIG. 1 shows a configuration of an endoscopic device according to the present embodiment. As shown in FIG. 1, the endoscopic device 1 of the present embodiment includes an endoscope 2, a light-source unit 3 connected to the endoscope 2, a main unit 4 including a camera control unit (hereinafter called CCU), and a monitor 5.

The endoscope 2 is an electronic endoscope having a long and thin inserted portion 11, an operating portion 12 connected to the proximal end of the inserted portion 11, and a universal cable 13 extending from the operating portion 12. An optical adaptor 2A can be attached to the distal end of the inserted portion 11.

A connector 14 is disposed at the leading end of the universal cable 13 extending from the operating portion 12, and this connector can be detachably attached to the light-source unit 3. A signal cable 15 extends from the connector 14. A connector 16 is disposed at the end of the signal cable 15, and the connector can be detachably attached to the main unit 4.

The inserted portion 11 of the endoscope 2 has a hard leading end 21 at the distal end, and a bending portion 22 adjacent to this leading end 21 that can bend freely. The inserted portion has a long flexible tubular portion 23 as well on the side of the proximal end of this bending portion 22. A user of the endoscopic device 1 can manipulate a knob for bending 24 disposed at the operating portion 12 to bend the bending portion 22.

Figure 2:
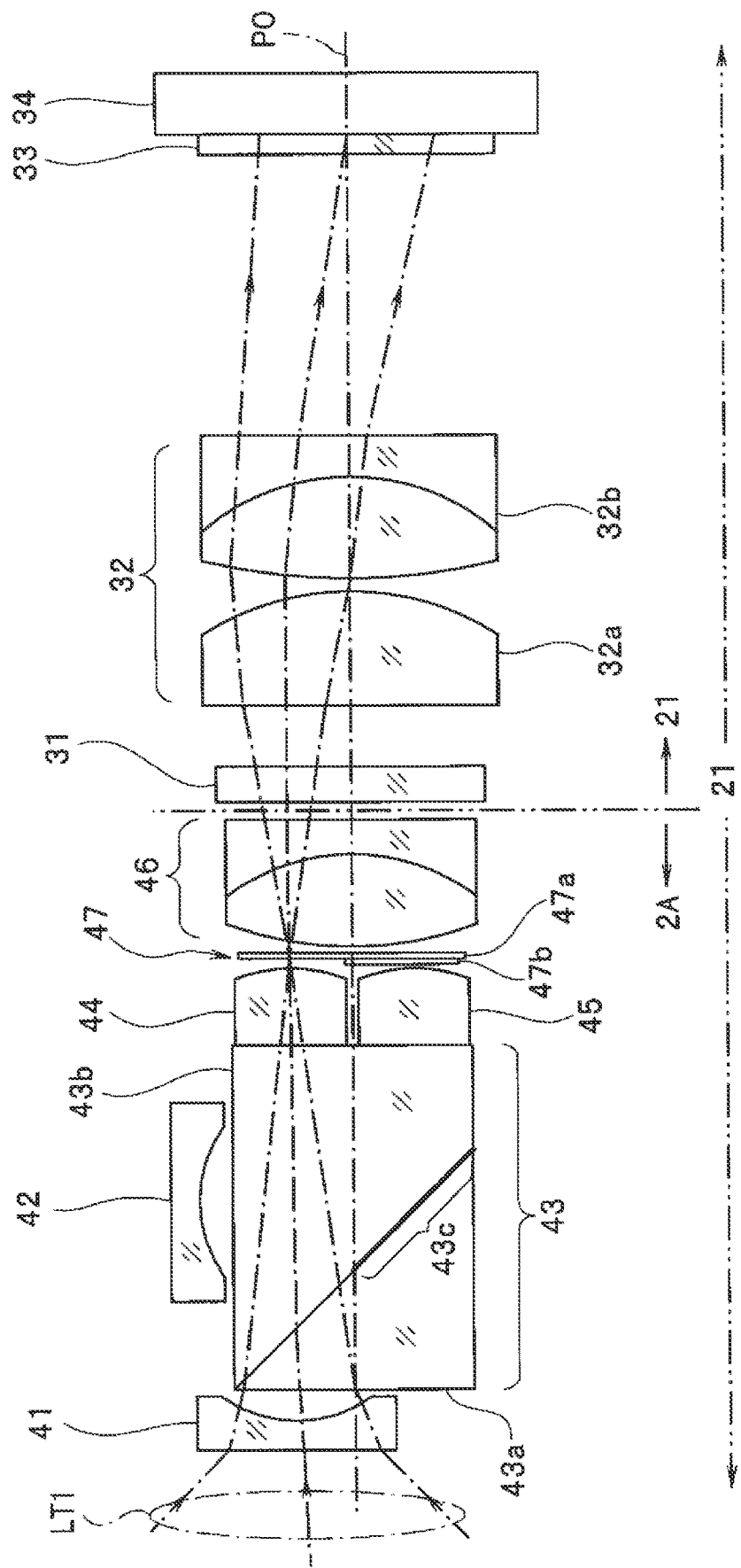
FIG. 2 shows the configuration of the optical system including a leading end of an inserted portion, to which an optical adaptor is attached, according to the embodiment.

The leading end 21 internally includes an image pickup device 34 (FIG. 2). An image pickup signal obtained by the image pickup device 34 is fed to the main unit 4 via a signal line passing through the inserted portion 11, the operating portion 12, the universal cable 13 and the signal cable 15.

The light-source unit 3 includes a light source, such as a lamp, and the light source generates illumination light. The illumination light enters the proximal-end face of an optical fiber (not illustrated) passing through the universal cable 13 and the inserted portion 11 and is emitted from the distal end of the inserted portion 11 to be applied to a subject for illumination.

The optical adaptor 2A can be attached to the leading end 21 of the inserted portion 11. The optical adaptor 2A is an adaptor for endoscope, and enables observation in two directions including the forward-viewing and the side-viewing.

The main unit 4 internally includes a controller as well as the CCU, and the controller controls the endoscopic device 1 as a whole. The main unit 4 includes a central processing unit (CPU), a ROM, a RAM and the like, which are not illustrated, and a user can perform various operations with an operating panel 4a. In order to implement the function corresponding to the operation, the main unit 4 executes a program in accordance with the function. The main unit 4 receives an image pickup signal from the endoscope 2 as an input, and outputs an image signal of the endoscopic image that is an image of the subject generated by the CCU to the monitor 5. Then the monitor 5 displays the endoscopic image.

By attaching the optical adaptor 2A to the leading end 21 of the inserted portion 11, the endoscope 2 enables observation in the two directions of the forward-viewing and the side-viewing.

Figure 2A:
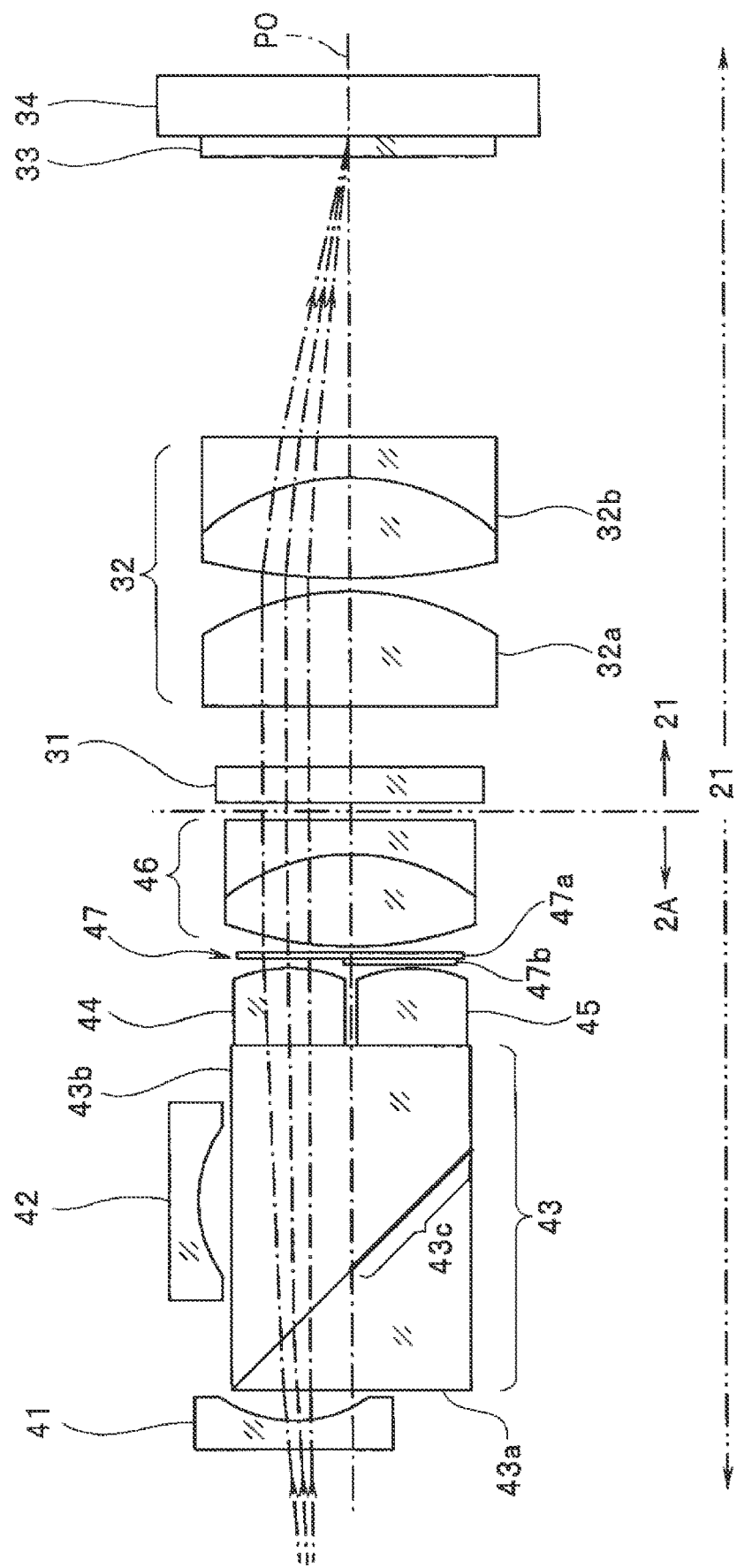
FIG. 2A shows the imaging of light in the configuration of the optical system including the leading end of the inserted portion, to which the optical adaptor is attached, according to the embodiment.

FIG. 2 shows the configuration of the optical system including the leading end 21 of the inserted portion 11, to which the optical adaptor 2A is attached. In FIG. 2, right of the two-dot chain line shows the optical system including the leading end 21 of the inserted portion 11, and left of the two-dot chain line shows the optical system of the optical adaptor 2A. FIG. 2A shows the imaging of light in the optical system including the leading end 21 of the inserted portion 11, to which the optical adaptor 2A is attached.

At the distal-end face of the leading end 21 of the inserted portion 11 that is round in cross section, a cover glass 31 of an observation window of the inserted portion 11 is disposed. In the leading end 21, an imaging optical system 32 and the image pickup device 34 having a cover glass 33 attached thereto are disposed. The imaging optical system is disposed behind the cover glass 31, and includes a plane-convex lens 32a and a cemented lens 32b. The cemented lens 32b is a lens obtained by joining a biconvex lens and a plane-concave lens.

The image pickup device 34 is disposed in the leading end 21 so that light of the subject image passing through the imaging optical system 32 forms an image on the imaging area of one image pickup device 34. The leading end 21 internally includes a hard member at the distal end, which is not illustrated. The cover glass 31, the image pickup device 34 and the like are fixed to the hard member at the distal end.

In the round-pillar shaped optical adaptor 2A, a concave lens 41 at the observation window for forward-viewing, a concave lens 42 at the observation window for side-viewing, a prism optical system 43, an imaging lens 44 for forward-viewing, an imaging lens 45 for side-viewing, an achromatizing lens 46, and a light-shielding portion 47 having a diaphragm are disposed. The optical adaptor 2A has a cylindrical hard member, and the concave lens 41 and the like are fixed to the hard member.

The concave lens 41 for forward-viewing makes up an incident optical system disposed at the front face of the round-pillar shaped optical adaptor 2A. The concave lens 42 for side-viewing makes up an incident optical system disposed at the lateral face of the round-pillar shaped optical adaptor 2A.

The concave lens 41 is disposed so that light is incident in the direction parallel or substantially parallel to the optical axis PO of the imaging optical system 32. The concave lens 42 is disposed so that light is incident in the direction orthogonal or substantially orthogonal to the optical axis PO of the imaging optical system 32.

That is, the concave lens 41 makes up the incident optical system configured so that, when the inserted portion 11 is inserted into the target to be examined, a light flux from a certain region of the subject is incident on the concave lens. The concave lens 42 makes up the incident optical system configured so that, when the inserted portion 11 is inserted into the target to be examined, a light flux from a region different from the certain region of the subject is incident on the concave lens.

Figure 3:
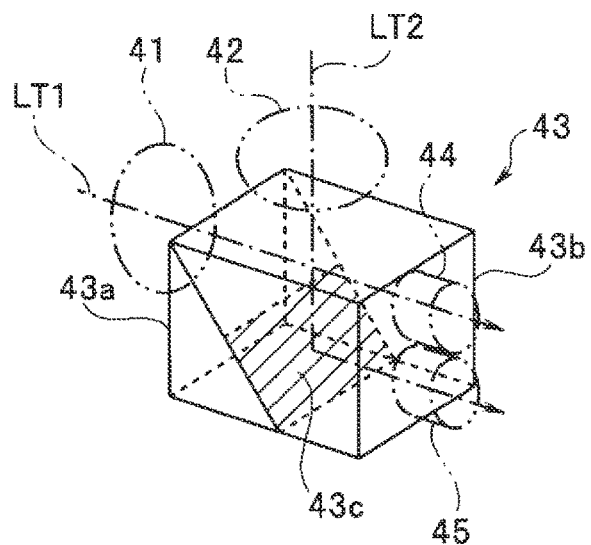
FIG. 3 is a perspective view of a prism optical system according to the embodiment.

The prism optical system 43 includes a triangular-prism shaped prism 43a that is a rectangular triangle in cross section, and a quadrangular-prism shaped glass member 43b having a obliquely cut one end. FIG. 3 is a perspective view of the prism optical system 43.

The inclined part of the prism 43a and the cut plane of the glass member 43b are joined. As shown in FIGS. 2 and 3, the prism optical system 43 is disposed in the optical adaptor 2A so that the prism 43a is disposed on the distal end side of the optical adaptor 2A and the glass member 43b is disposed on the proximal end side of the optical adaptor 2A. The prism optical system 43 is disposed in the optical adaptor 2A so that one of the planes of the prism 43a faces the concave lens 41 and one of the faces of the glass member 43b faces the concave lens 42.

A mirror region 43c is disposed at a part of the inclined part of the prism 43a or of the cut plane of the glass member 43b, and the mirror region reflects light. That is, the mirror region 43c is disposed at a partial region of the joined plane of the inclined part of the prism 43a and the cut plane of the glass member 43b. The mirror region 43c is formed in the prism optical system 43 by evaporation of aluminum, and is formed on one of the surfaces of the inclined part of the prism 43a and the cut plane of the glass member 43b.

In the optical adaptor 2A, the concave lens 41 for forward-viewing is disposed at a position so that the incident light is emitted toward a region other than the mirror region 43c, and the concave lens 42 for side-viewing is disposed at a position so that the incident light is emitted toward the mirror region 43c.

The prism optical system 43 has a prism, so that the light flux LT1 from the concave lens 41 passes through the prism optical system 43 and is emitted toward the imaging optical system 32 and the light flux LT2 from the concave lens 42 is reflected from the prism of the prism optical system 43 and is emitted toward the imaging optical system 32.

Therefore as shown in FIG. 3, the light flux LT1 from the concave lens 41 and the light flux LT2 from the concave lens 42 intersect in the prism optical system 43.

That is, the prism optical system 43 makes up an intersecting optical system, in which the light flux LT1 passing through the concave lens 41 and the light flux LT2 passing through the concave lens 42 intersect and are emitted to a predetermined region.

Each of the cross section of the light flux LT1 and the cross section of the light flux LT2 in the directions orthogonal to their optical axes has an area. The light flux LT1 and the light flux LT2 in this embodiment intersect so that their optical axes intersect. The light flux LT1 and the light flux LT2 may intersect so that their optical axes do not intersect. In that case, the light flux LT1 and the light flux LT2 partially intersect.

In other words, the prism optical system 43 as the intersecting optical system may be configured so that the incident light flux LT1 and the light flux LT2 intersect at least partially, and the light flux LT1 and the light flux LT2 then are emitted toward the imaging optical system 32.

On the proximal-end side of the prism optical system 43, two imaging lenses 44 and 45 are bonded, and these imaging lenses are plane-convex lenses. The imaging lens 44 is a round-pillar shaped plane-convex lens, and makes up the optical system for forward-viewing. The light flux from the concave lens 41 passing through a region other than the mirror region 43c of the prism optical system 43 is incident on this imaging lens. The imaging lens 45 is a round-pillar shaped plane-convex lens, and makes up the optical system for side-viewing. The light flux from the concave lens 42 reflected from the mirror region 43c of the prism optical system 43 is incident on this imaging lens.

On the proximal-end side of the imaging lenses 44 and 45, the achromatizing lens 46 is disposed. The achromatizing lens includes a biconvex lens and a plane-concave lens that are joined.

As stated above, the imaging lens 44 is disposed at a position so that light from the concave lens 41 for forward-viewing passing through the prism optical system 43 is incident on the imaging lens, and the light is emitted to the achromatizing lens 46. The imaging lens 45 is disposed at a position so that light from the concave lens 42 for side-viewing reflected from the mirror region 43c of the prism optical system 43 is incident on the imaging lens, and the light is emitted to the achromatizing lens 46.

Therefore as shown in FIG. 3, when being incident on the prism optical system 43, the light flux LT1 from the concave lens 41 for forward-viewing passes through a part other than the mirror region 43c and is emitted from the prism optical system 43 toward the imaging lens 44. Then, the imaging lens 44 emits the light from the front of the inserted portion 11 toward the achromatizing lens 46.

When being incident on the prism optical system 43, the light flux LT2 from the concave lens 42 for side-viewing is reflected from the mirror region 43c at right angles, and is emitted from the prism optical system 43 toward the imaging lens 45. Then, the imaging lens 45 emits the light from the side of the inserted portion 11 toward the achromatizing lens 46.

The light flux LT1 from the concave lens 41 and the light flux LT2 from the concave lens 42 are incident in the prism optical system 43. The light flux LT1 passes through a part other than the mirror region 43c of the prism optical system 43 and is emitted from the prism optical system 43 toward the imaging lens 44.

The light flux LT1 and the light flux LT2 intersect in the prism optical system 43. The light flux LT2 is then reflected from the mirror region 43c and is emitted from the prism optical system 43 toward the imaging lens 45.

Between the two imaging lenses 44, 45 and the achromatizing lens 46, the light-shielding portion 47 is disposed.

Figure 4:
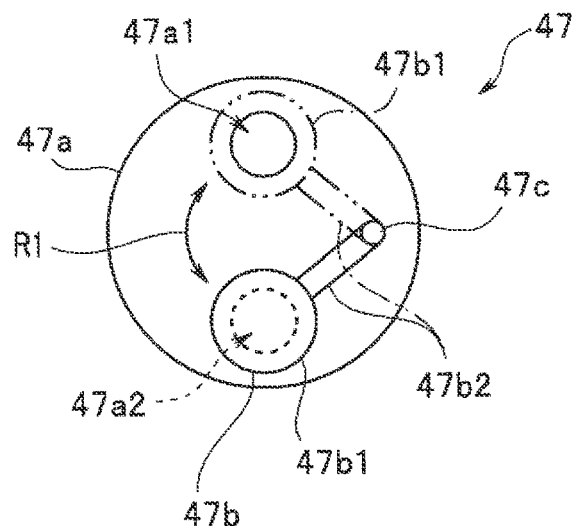
FIG. 4 shows the configuration of a light-shielding portion according to one embodiment.

FIG. 4 shows the configuration of the light-shielding portion 47. The light-shielding portion 47 includes a disk-shaped diaphragm plate 47a, a light-shielding member 47b and a shaft member 47c to rotate the light-shielding member 47b.

The diaphragm plate 47a has two round holes 47a1 and 47a2. The hole 47a1 is formed in the diaphragm plate 47a at a position along the optical path of the light flux LT1 emitted from the imaging lens 44. The hole 47a2 is formed in the diaphragm plate 47a at a position along the optical path of the light flux LT2 emitted from the imaging lens 45.

The light-shielding member 47b includes a disk-shaped light-shielding plate 47b1 and an arm 47b2 having one end connected to and extending from the light-shielding plate 47b1. The other end of the arm 47b2 is connected and fixed to the shaft member 47c.

The shaft member 47c is connected to a driving mechanism not illustrated. The driving mechanism is configured to rotate the shaft member 47c around the axis within a predetermined range as indicated with arrow R1.

The shaft member 47c is driven by a driving means, such as an electrical magnet. The driving means is driven in accordance with a user's predetermined operation with the operating panel 4a. A driving signal to drive the electrical magnet or the like is supplied to the optical adaptor 2A in accordance with the operation by the user with the operating panel 4a via a signal line inserted into the inserted portion 11 and via a contact between the leading end 21 of the inserted portion 11 and the optical adaptor 2A. The electrical magnet or the like in the optical adaptor 2A is then driven to rotate the shaft member 47c. As a result, the light-shielding plate 47b1 is driven so as to selectively cover any one of the two round holes 47a1 and 47a2. FIG. 4 shows the light-shielding plate 47b1 at the position to cover the hole 47a2.

As shown in FIG. 4, when the light-shielding plate 47b1 is at the position to cover the hole 47a2 as indicated with the solid line, the light flux LT1 for forward-viewing is incident on the achromatizing lens 46. When the light-shielding plate 47b1 is at the position to cover the hole 47a1 as indicated with the two-dot chain line, the light flux LT2 (FIG. 6) for side-viewing is incident on the achromatizing lens 46.

That is, the light-shielding portion 47 is disposed at a predetermined region and includes diaphragms for the light flux LT1 and the light flux LT2. The light-shielding portion shields one of the light flux LT1 and the light flux LT2 emitted from the prism optical system 43 selectively.

Figure 5:
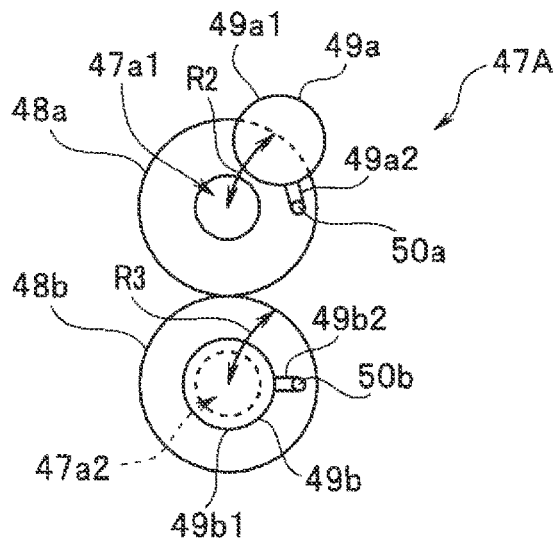
FIG. 5 shows the configuration of a light-shielding portion having a different configuration from FIG. 4 according to one embodiment.

The light-shielding portion 47 may have a configuration other than that shown in FIG. 4. FIG. 5 shows the configuration of a light-shielding portion 47A that is different from FIG. 4. The light-shielding portion 47A includes two disk-shaped diaphragm plates 48a and 48b, two light-shielding members 49a and 49b, and two shaft members 50a and 50b to rotate the two light-shielding members 49a and 49b.

The diaphragm plate 48a is formed at a position along the optical path of the light flux LT1 from the front of the optical adaptor 2A and emitted from the imaging lens 44. The diaphragm plate 48a has a hole 47a1. The diaphragm plate 48b is formed at a position along the optical path of the light flux LT2 from the side of the optical adaptor 2A and emitted from the imaging lens 45. The diaphragm plate 48b has a hole 47a2.

The light-shielding member 49a includes a disk-shaped light-shielding plate 49a1 and an arm 49a2 having one end connected to and extending from the light-shielding plate 49a1. The other end of the arm 49a2 is connected and fixed to the shaft member 50a. As indicated with arrow R2, the shaft member 50a is rotatable around the axis within a predetermined range.

The light-shielding member 49b includes a disk-shaped light-shielding plate 49b1 and an arm 49b2 having one end connected to and extending from the light-shielding plate 49b1. The other end of the arm 49b2 is connected and fixed to the shaft member 50b. As indicated with arrow R3, the shaft member 50b is rotatable around the axis within a predetermined range.

Each shaft member 50a, 50b is driven by an electrical magnet or the like that is driven in accordance with a user's predetermined operation with the operating panel 4a. A driving signal to drive the electrical magnet or the like is supplied to the optical adaptor 2A in accordance with the operation by the user with the operating panel 4a via a signal line inserted into the inserted portion 11 and via a contact between the leading end 21 of the inserted portion 11 and the optical adaptor 2A. The electrical magnet or the like in the optical adaptor 2A is then driven to rotate the shaft members 50a and 50b individually. As a result, the shaft members 50a and 50b are driven so that when one of the light-shielding members 49a and 49b covers their corresponding hole 47a1 or 47a2, the other light-shielding member does not cover the hole. FIG. 5 shows the light-shielding plate 49a1 at the position not to cover the hole 47a1 and the light-shielding plate 49b1 at the position to cover the hole 47a2.

Figure 6:
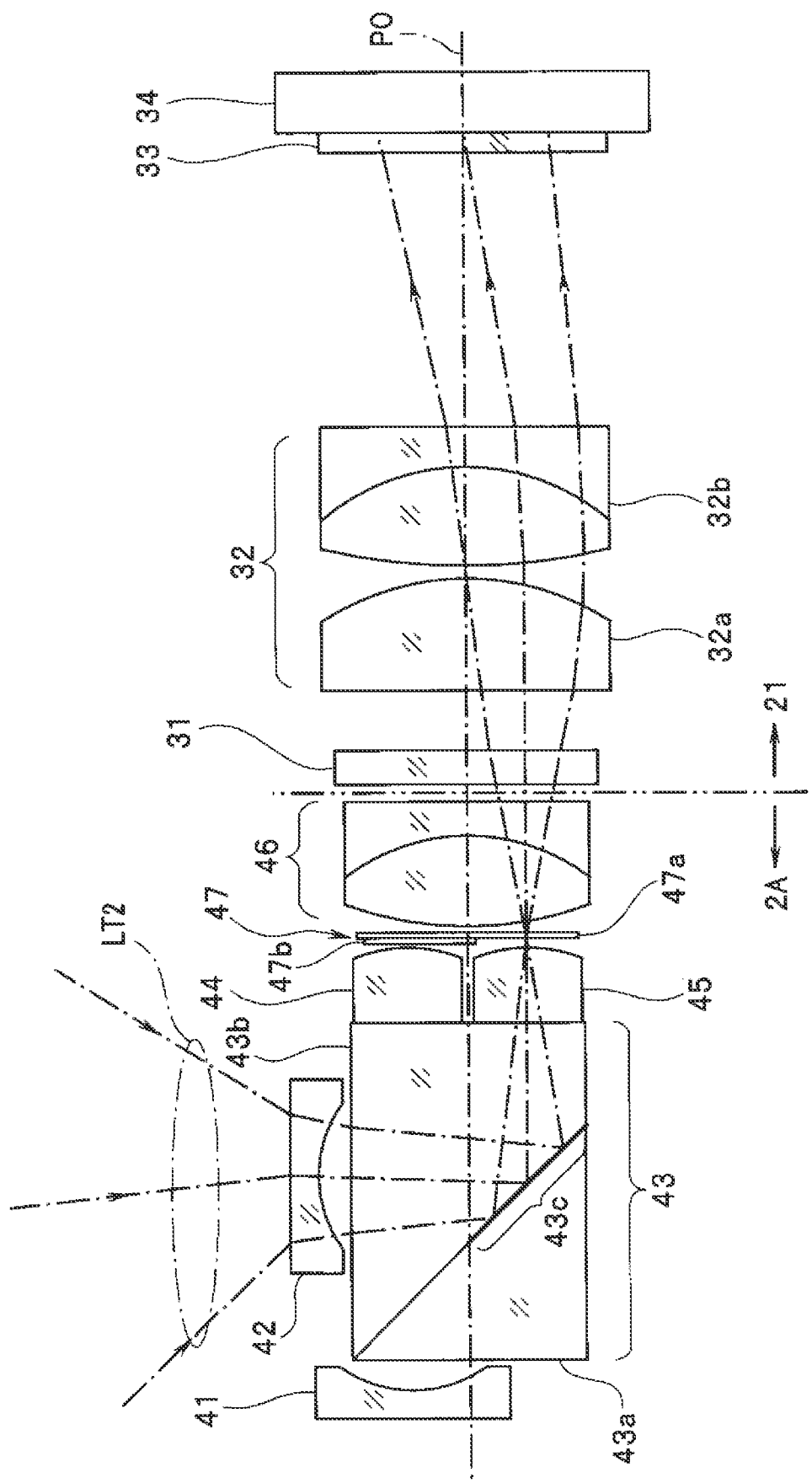
FIG. 6 shows the configuration of the optical system including the leading end of the inserted portion, to which the optical adaptor is attached, and FIG. 6 further shows the optical path from a concave lens for side-viewing when the light-shielding portion functions to transmit the optical path of the light flux from the concave lens.

As shown in FIG. 5, when the light-shielding plate 49a1 is at the position not to cover the hole 47a1 and the light-shielding plate 49b1 is at the position to cover the hole 47a2, the light flux LT1 from the front is incident on the achromatizing lens 46. On the contrary, when the light-shielding plate 49b1 is at the position not to cover the hole 47a2 and the light-shielding plate 49a1 is at the position to cover the hole 47a2, the light flux LT2 from the side is incident on the achromatizing lens 46 (FIG. 6).

That is, the two light-shielding plates 49a1 and 49b1 driven independently may shield the two holes 47a1 and 47a2.

Light from the optical adaptor 2A is incident on the imaging optical system 32 in the leading end 21. Light from the front of the inserted portion 11 and light from the side of the inserted portion are incident on the imaging lens 32.

Although the light flux LT1 from the front and the light flux LT2 from the side travel along different optical paths, the imaging optical system 32 forms images of the light flux LT1 from the front and of the light flux LT2 from the side at a common region of the imaging area of one image pickup device 34.

When the light-shielding portion 47 functions to shield the light flux from the concave lens 42 for side-viewing and to transmit the optical path of the light flux LT1 from the concave lens 41 for forward-viewing, the light flux from the concave lens 41 travels along the optical path indicated with the dot-and-dash line and forms an image on the imaging area of the image pickup device 34 as shown in FIG. 2A.

FIG. 6 shows the configuration of the optical system including the leading end 21 of the inserted portion 11, to which the optical adaptor 2A is attached, and this drawing shows the optical path from the concave lens 42 for side-viewing when the light-shielding portion 47 functions to transmit the optical path of the light flux LT2 from the concave lens 42.

Figure 6A:
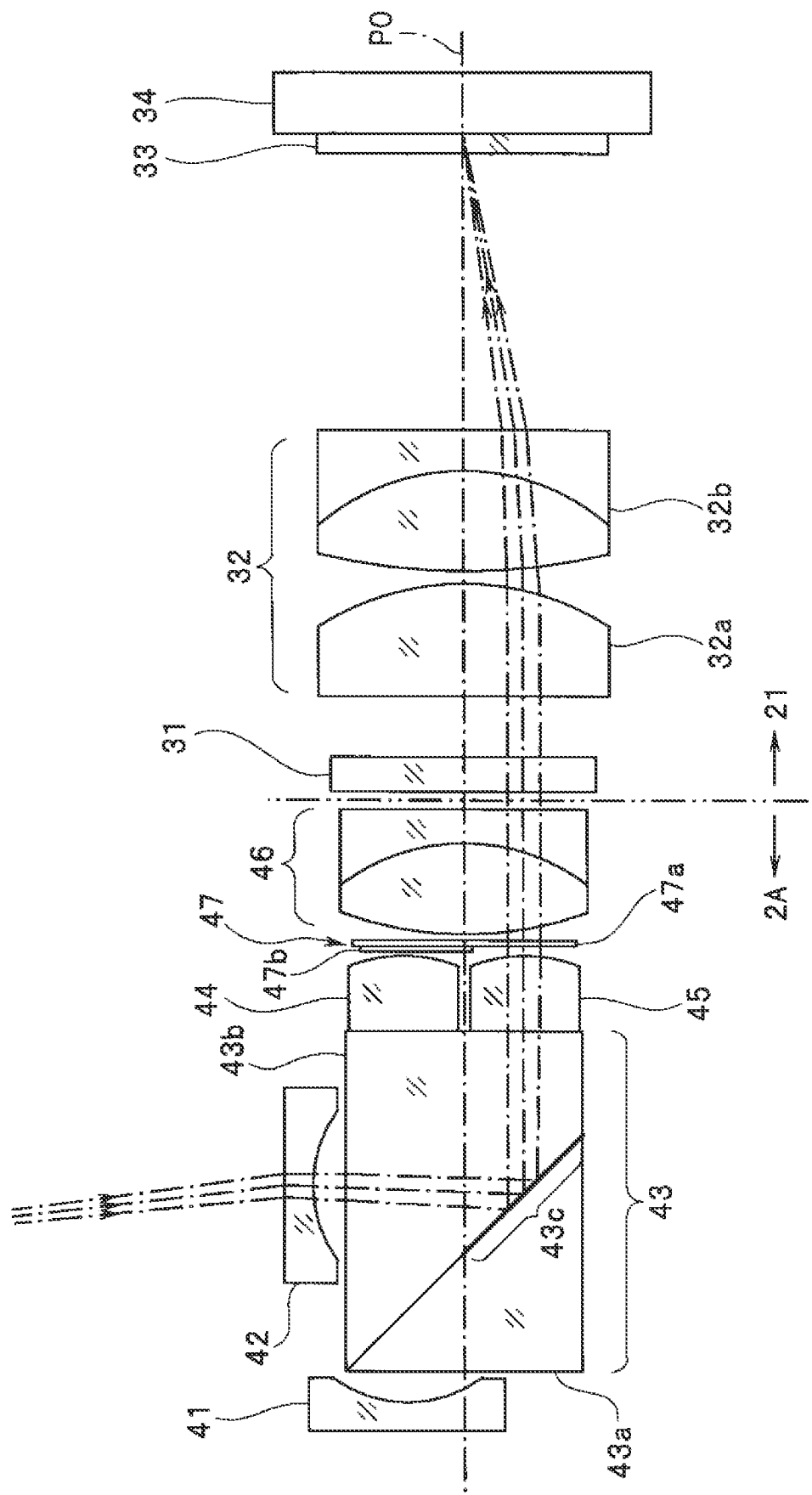
FIG. 6A shows the imaging of light in the configuration of the optical system including the leading end of the inserted portion, to which the optical adaptor is attached, and FIG. 6A further shows the optical path from the concave lens for side-viewing when the light-shielding portion functions to transmit the optical path of the light flux from the concave lens.

FIG. 6A shows the imaging of light in the configuration of the optical system including the leading end 21 of the inserted portion 11, to which the optical adaptor 2A is attached, and this drawing shows the optical path from the concave lens 42 for side-viewing when the light-shielding portion 47 functions to transmit the optical path of the light flux LT2 from the concave lens 42.

When the light-shielding portion 47 functions to transmit the light flux LT2 from the concave lens 42 for side-viewing, the light flux LT2 from the concave lens 42 travels along the optical path indicated with the dot-and-dash line and forms an image on the imaging area of the image pickup device 34 as shown in FIG. 6A.

The imaging optical system 32 is disposed closer to the subject or the image pickup device 34 than the light-shielding portion 47 is, and forms images of the light flux LT1 passing through the concave lens 41 for forward-viewing and of the light flux LT2 passing through the concave lens 42 for side-viewing on a common region on the imaging area of the image pickup device 34. Since the images of the subject are projected on the common region of the imaging area of the image pickup device 34, a more precise image of the subject can be obtained from the image pickup signal output from the image pickup device 34.

A conventional endoscope capable of observing in two directions of the forward-viewing and the side-viewing can be configured to switch two images and project the images on a common region on the imaging area of one image pickup device. In such a conventional endoscope, however, the light flux in each direction from the front and the side will be thick, and so the outer diameter of the lens at each observation window has to increase and these two lenses at the observation windows have to be separated in position. As a result, the outer diameters of the optical adaptor and of the leading end of the inserted portion of the endoscope will increase.

On the contrary, according to the endoscope 2 including the optical adaptor 2A of the present embodiment as stated above, the light flux LT1 passing through the concave lens 41 for forward-viewing and the light flux LT2 passing through the concave lens 42 for side-viewing intersect in the prism optical system 43. With this configuration, the lenses at the two observation windows with a larger outer diameter can be disposed closer. As a result, the optical adaptor and the leading end of the inserted portion of the endoscope can have smaller outer diameters.

As stated above, according to the endoscope 2 as stated above, the endoscope is configured to switch two images in the two directions for forward-viewing and side-viewing and project the images on a common region of the imaging area of one image pickup device to obtain a more precise image, and the optical adaptor and the leading end of the inserted portion of the endoscope can have smaller outer diameters.

Therefore the present embodiment can provide an adaptor for endoscope, the endoscope being configured to switch two optical images from different directions and project the images on a common region of the imaging area of the image pickup device, and the adaptor for endoscope can have a smaller diameter at the leading end of the optical device.

The following describes modified examples of the embodiment as stated above.

Modified Example 1

Modified Example 1 relates to a modified example of the prism optical system 43.

In the embodiment as stated above, the prism optical system 43 includes a triangular-prism shaped prism 43a that is a rectangular triangle in cross section, and a quadrangular-prism shaped glass member 43b having a obliquely cut one end. The prism optical system of Modified Example 1 includes a cuboid glass member and a quadrangular-prism shaped glass member having one end obliquely cut at a predetermined angle.

Figure 7:
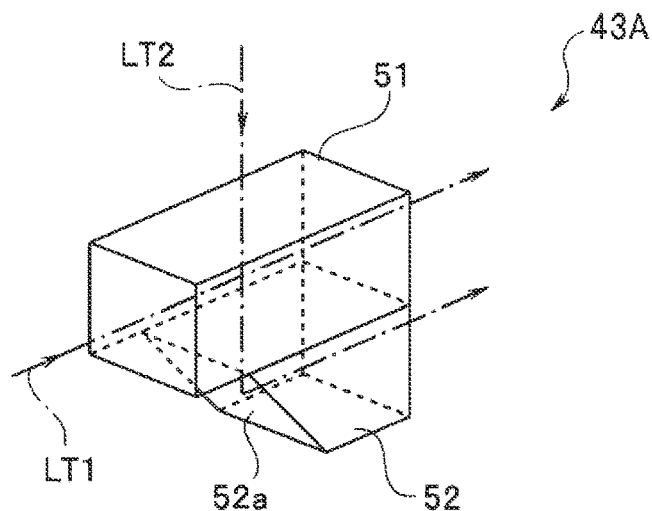
FIG. 7 is a perspective view of the prism optical system of Modified Example 1 of the embodiment.

FIG. 7 is a perspective view of the prism optical system of Modified Example 1 of the embodiment. The prism optical system 43A of Modified Example 1 includes a cuboid glass member 51 and a quadrangular-prism shaped glass member 52 having one end obliquely cut at a predetermined angle, at 45 degrees in this example. These glass members are bonded with adhesive. The glass members 51 and 52 are disposed so that the cuboid glass member 51 has a longitudinal axis that is parallel to the optical axis of the light flux from the concave lens 41 and the quadrangular-prism shaped glass member 52 also has a longitudinal axis that is parallel to the optical axis of the light flux from the concave lens 41. The cut plane 52a of the glass member 52 is a mirror region formed by evaporation of aluminum.

In FIG. 7, when the not-illustrated light-shielding portion 47 functions to transmit the light flux LT1 from the concave lens 41 for forward-viewing, the light flux LT1 from the concave lens 41 passes through the glass member 51 along the optical path indicated with the dot-and-dash line in FIG. 7 and forms an image on a common region on the imaging area of the image pickup device 34 through the imaging optical system 32.

When the light-shielding portion 47 functions to transmit the light flux LT2 from the concave lens 42 for side-viewing, the light flux LT2 from the concave lens 42 passes through the glass member 51 along the optical path indicated with the dot-and-dash line in FIG. 7 and is incident on the glass member 52. Then the light flux is reflected from the cut plane 52a and forms an image on a common region on the imaging area of the image pickup device 34 through the imaging optical system 32.

A similar effect to that from the embodiment as stated above can be obtained from the prism optical system 43A of Modified Example 1 as well.

Modified Example 2

Modified Example 2 relates to a modified example of the prism optical system 43.

Similarly to Modified Example 1, the prism optical system of Modified Example 2 includes a cuboid glass member and a quadrangular-prism shaped glass member having one end obliquely cut at a predetermined angle.

Figure 8:
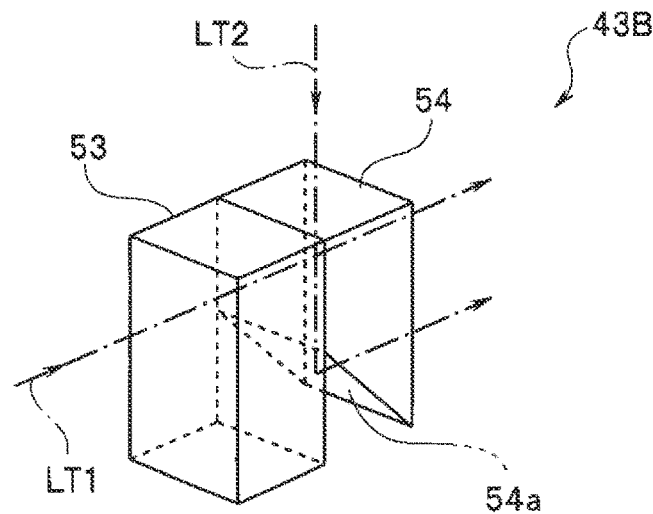
FIG. 8 is a perspective view of the prism optical system of Modified Example 2 of the embodiment.

FIG. 8 is a perspective view of the prism optical system of Modified Example 2 of the embodiment. The prism optical system 43B of Modified Example 2 includes a cuboid glass member 53 and a quadrangular-prism shaped glass member 54 having one end obliquely cut at a predetermined angle, at 45 degrees in this example. These glass members are bonded with adhesive. The glass members 53 and 54 are disposed so that the cuboid glass member 53 has a longitudinal axis that is orthogonal to the optical axis of the light flux from the concave lens 41 and the quadrangular-prism shaped glass member 54 also has a longitudinal axis that is orthogonal to the optical axis of the light flux from the concave lens 41. The cut plane 54a of the glass member 54 is a mirror region formed by evaporation of aluminum.

In FIG. 8, when the not-illustrated light-shielding portion 47 functions to transmit the light flux LT1 from the concave lens 41 for forward-viewing, the light flux LT1 from the concave lens 41 passes through the glass members 53 and 54 along the optical path indicated with the dot-and-dash line in FIG. 8 and forms an image on a common region on the imaging area of the image pickup device 34 through the imaging optical system 32.

When the light-shielding portion 47 functions to transmit the light flux LT2 from the concave lens 42 for side-viewing, the light flux LT2 from the concave lens 42 is incident on the glass member 54 and is reflected from the cut plane 54a along the optical path indicated with the dot-and-dash line in FIG. 8 and forms an image on a common region on the imaging area of the image pickup device 34 through the imaging optical system 32.

A similar effect to that from the embodiment as stated above can be obtained from the prism optical system 43B of Modified Example 2 as well.

Modified Example 3

Modified Example 3 relates to the imaging lenses 44 and 45 at the optical adaptor 2A.

The two imaging lenses 44 and 45 at the optical adaptor 2A of the embodiment as stated above are round-pillar shaped plane-convex lenses. Modified Example 3 includes decentered lenses as the two imaging lenses.

Figure 9:
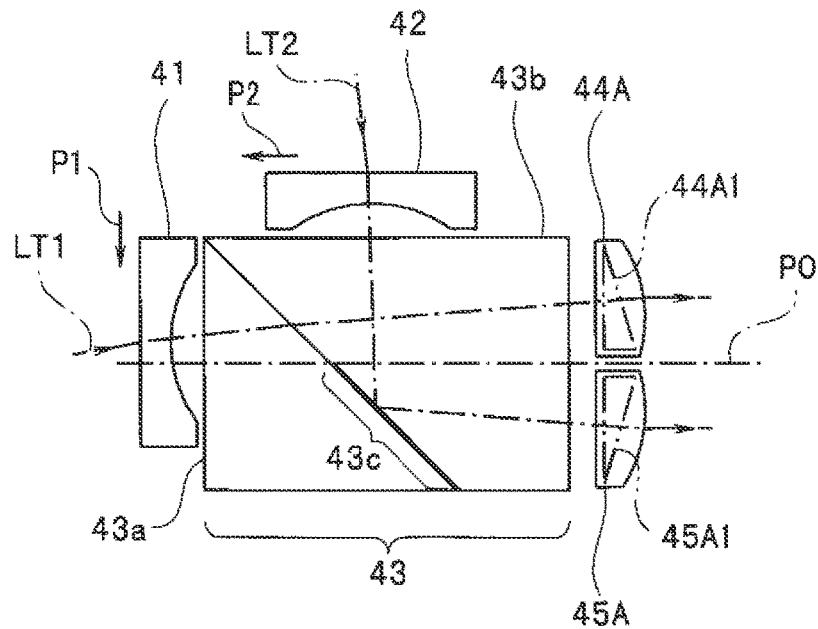
FIG. 9 shows a partial configuration of the optical system of the optical adaptor, relating to Modified Example 3 of the embodiment.

FIG. 9 shows the configuration of the optical system of the optical adaptor 2A partially, relating to Modified Example 3 of the embodiment. FIG. 9 omits the achromatizing lens 46 and the light-shielding portion 47.

In Modified Example 3, like parts are referred to by like numerals of the embodiment as stated above, and the following describes different configurations only.

As shown in FIG. 9, the imaging lens 44A for forward-viewing and the imaging lens 45A for side-viewing of Modified Example 3 are decentered lenses. These decentered lenses make up a deflecting optical system.

Figure 10:
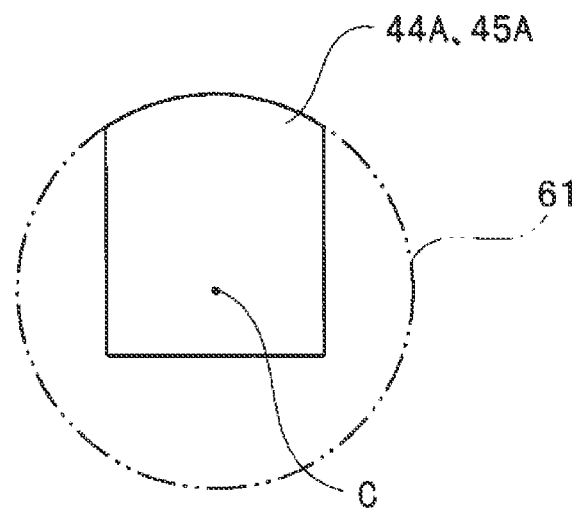
FIG. 10 shows the configuration of a decentered lens, relating to Modified Example 3 of the embodiment.

FIG. 10 shows the configuration of a decentered lens. The imaging lenses 44A and 45A have a shape obtained by cutting out a part of a plane-convex lens 61 indicated with the two-dot and chain line. Each of the imaging lenses 44A and 45A has a shape obtained by cutting a part of the plane-convex lens 61 including the center axis C.

As shown in FIG. 10, each of the imaging lenses 44A and 45A as a plane-convex lens is disposed on the proximal-end side of the prism optical system 43 so that its planar part faces one of the faces of the prism optical system 43, its convex part faces the achromatizing lens 46, and their central axes C are close to each other.

As stated above, the optical adaptor 2A includes the imaging lens 44A as a decentered lens to deflect the light flux LT1 emitted from the prism optical system 43 and the imaging lens 45A as a decentered lens to deflect the light flux LT2 emitted from the prism optical system 43. After passing through the imaging lenses 44A and 45A, respectively, the light flux LT1 and the light flux LT2 are incident on the imaging optical system 32.

Such a decentered lens as the imaging lens 44A allows the light flux LT1 from the front to be directed to the light-shielding portion 47 and the achromatizing lens 46 so that an image of the light flux LT1 from the front can be formed on a common region on the imaging area of the image pickup device 34 when the concave lens 41 is disposed closer to the optical axis PO of the imaging optical system 32 as indicated with arrow P1. This can realize a smaller outer diameter of the optical adaptor 2A.

Such a decentered lens as the imaging lens 45A allows the light flux LT2 from the side to be directed to the light-shielding portion 47 and the achromatizing lens 46 so that an image of the light flux LT2 from the side can be formed on a common region on the imaging area of the image pickup device 34 when the concave lens 42 is disposed closer to the distal end of the optical adaptor 2A as indicated with arrow P2.

A similar effect to that from the embodiment as stated above can be obtained from Modified Example 3 as well.

The imaging lenses 44A and 45A may be an optical system including prisms 44A1 and 45A1 as indicated with the two-dot chain line so as to deflect the light instead of the decentered lenses.

Modified Example 4

The embodiment and the modified examples as stated above relate to an optical adaptor for endoscope enabling forward-viewing and side-viewing. Modified Example 4 relates to an optical adaptor enabling observation from two different directions from the obliquely front.

Since the leading end of the inserted portion of the endoscope of Modified Example 4 has the same configuration as that of the leading end 21 of the inserted portion 11 of the endoscope 2 of the embodiment as stated above, their descriptions are omitted. The following describes the configuration of the optical adaptor.

Figure 11:
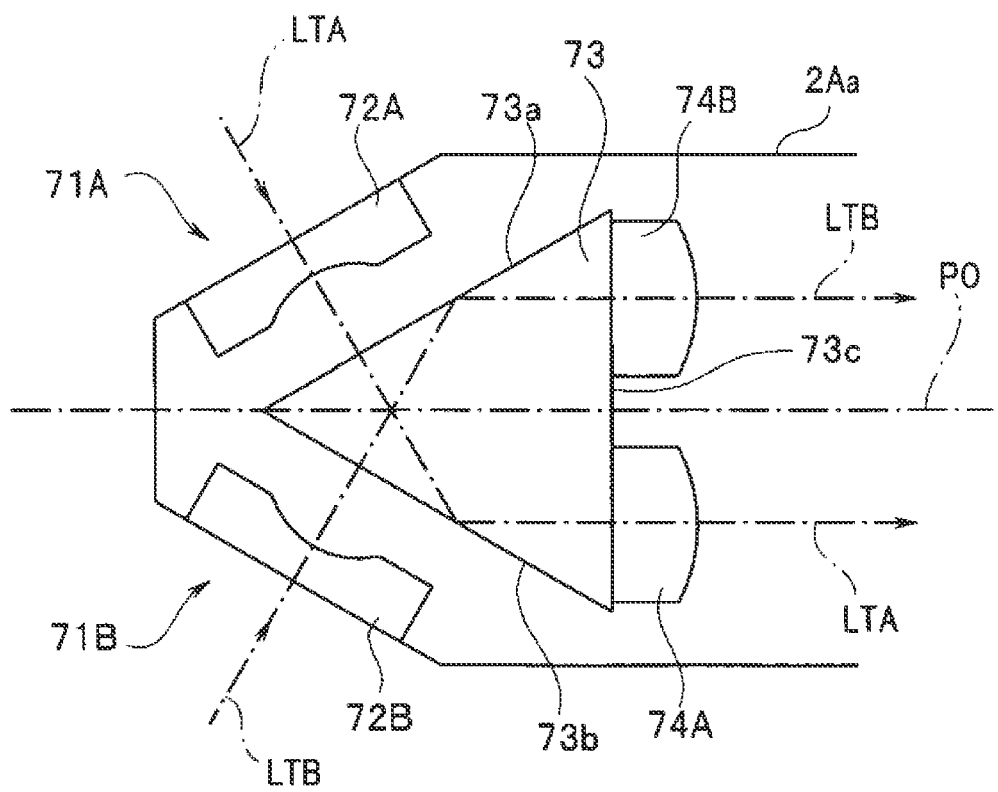
FIG. 11 is a schematic cross-sectional view of the configuration of the optical adaptor relating to Modified Example 4 of the embodiment.

FIG. 11 is a schematic cross-sectional view of the configuration of the optical adaptor relating to Modified Example 4. FIG. 11 omits the achromatizing lens 46 and the light-shielding portion 47.

The optical adaptor 2Aa of Modified Example 4 is attached to the leading end 21 of the inserted portion 11. This optical adaptor includes an observation window 71A for observation in the direction inclined at a predetermined angle relative to the optical axis PO of the imaging optical system 32 of the inserted portion 11, at 60 degrees in this example, and an observation window 71B for observation in the direction inclined at a predetermined angle relative to the axis of the inserted portion 11, at −60 degrees in this example.

The observation window 71A includes a concave lens 72A as an incident optical system. The observation window 71B includes a concave lens 72B as an incident optical system. That is, the concave lens 72A is disposed so that light LTA is incident at a predetermine angle (60 degrees) relative to the optical axis PO of the imaging optical system 32 and the concave lens 72B is disposed so that light LTB is incident at a predetermine angle (−60 degrees) relative to the optical axis PO of the imaging optical system 32.

In the optical adaptor 2Aa, the prism optical system 73 that is a regular triangle in cross section is disposed so that its first face 73a faces a concave lens 72A and its second face 73b faces a concave lens 72B. Imaging lenses 74A and 74B that are plane-convex lenses are bonded with adhesive to the third face 73c of the prism optical system 73.

The light LTA incident on the concave lens 72A is incident on the first face 73a of the prism optical system 73, and is total-reflected from the inside of the second face 73b. Then the light is emitted from the third face 73c and is incident on the imaging lens 74A.

The light LTB incident on the concave lens 72B is incident on the second face 73b of the prism optical system 73, and is total-reflected from the inside of the first face 73a. Then the light is emitted from the third face 73c and is incident on the imaging lens 74B.

Also in this modified example, the light LTA from the concave lens 72A and the light LTB from the concave lens 72B intersect in the prism optical system 73, and then are incident on the imaging lenses 74A and 74B, respectively. This can realize a small diameter of the optical adaptor 2Aa.

A similar effect to that from the embodiment as stated above can be obtained from Modified Example 4 as well.

Modified Example 5

The embodiment and Modified Examples 1 to 4 as stated above are configured to attach the optical adaptor 2A, 2Aa to the leading end 21 of the inserted portion 11 of the endoscope 2 to implement an optical device to switch two optical images from different directions and project the images on a common region of the imaging area of the image pickup device. The endoscope 2 may include the configuration of these optical adaptors built in the leading end 21 of the inserted portion 11 of the endoscope 2 and may implement the optical device without an optical adaptor to switch two optical images from different directions and project the images on a common region of the imaging area of the image pickup device 34.

As stated above, the embodiment and the modified examples as stated above can provide an optical device configured to switch a plurality of images of a subject from different directions and project these images on a common region of the imaging area of the image pickup device, the leading end of the optical device having a smaller diameter.

The present invention is not limited to the embodiments as stated above, and can be changed and modified variously without changing the scope of the present invention.

What is claimed is:

1. An endoscope comprising:
   a first concave lens, a first light flux from a first region of a subject being incident on the first-concave lens;
   a second concave lens, a second light flux from a second region of the subject being incident on the second concave lens, the second light flux being in a direction orthogonal to the first light flux, the second region being different from the first region;
   a prism comprising a mirror region, the first light flux and the second light flux each being incident on the prism, the first light flux and the second light flux passing through the prism at an intersecting portion of the prism, the second light flux being reflected by the mirror region after passing through the intersecting portion, the first light flux and the second light flux being emitted from the prism to a predetermined region;
   a light-shield disposed at the predetermined region, the light-shield comprising two holes through which the first light flux and the second light flux pass through, respectively, the light-shield being configured to selectively shield one of the two holes;
   an image sensor comprising an imaging area; and
   an imaging lens disposed closer to the image sensor than the light-shield is, the imaging lens being configured to form images of the first light flux passing through the first concave lens and of the second light flux passing through the second concave lens at a common region of the imaging area;

wherein the first concave lens is disposed such that the first light flux from the first concave lens being incident in a direction substantially parallel to the optical axis of the imaging lens and directed toward a center of the image sensor, the first light flux being disposed only on a first side of an optical axis of the imaging lens; and the second concave lens is disposed so that the second light flux from the second concave lens being incident in a direction substantially orthogonal to the optical axis of the imaging lens and directed toward the center of the image sensor, the second light flux being disposed only on a second side of the optical axis of the imaging lens, the first side and the second side are offset in a direction perpendicular to the optical axis of the imaging lens with the second side being opposite to the first side relative to the optical axis;

the endoscope further comprising:

a first decentered lens disposed on the first side of the optical axis of the imaging lens, the first decentered lens being configured to deflect the first light flux such that a part of the first light flux emitted from the prism and passing through a center of one of the two holes reaches a center of an image formed on the image sensor, the part of the first light flux being inclined with respect to the optical axis of the imaging lens; and a second decentered lens disposed on the second side of the optical axis of the imaging lens, the second decentered lens being configured to deflect the second light flux such that a part of the second light flux emitted from the prism and passing through a center of an other of the two holes reaches the center of the image formed on the image sensor, the part of the second light flux being inclined with respect to the optical axis of the imaging lens;

wherein the first light flux passes through the first decentered lens, the one of the two holes of the light shield and then is incident on the imaging lens, the second light flux passes through the second decentered lens, the other of the two holes of the light shield and then is incident on the imaging lens.

2. The endoscope according to claim 1, wherein each of the first decentered lens and the second decentered lens includes a prism.

3. The endoscope according to claim 1, wherein the light-shield includes a diaphragm movable between a first position to shield the first light flux and a second position to shield the second light flux.

4. The endoscope according to claim 1, wherein the prism is disposed such that the first light flux is emitted toward a region of the prism other than the mirror region; and the second concave lens is disposed such that the second light flux is emitted toward the mirror region.

5. The endoscope according to claim 1, wherein the first concave lens is disposed such that the first light flux is incident in a direction parallel to the optical axis of the imaging lens; and the mirror region is disposed in a region of the prism such that the first light flux is not incident on the mirror region.

6. The endoscope according to claim 1, wherein the prism comprising a cuboid portion and a quadrangular-prism shaped portion, the quadrangular-prism shaped portion having an end surface obliquely formed at a predetermined angle;

the mirror region is disposed on the end surface;

the first light flux passes through the cuboid portion and being emitted to the predetermined region;

the second light flux passes through the cuboid portion, is subsequently incident on the end surface, reflected by the mirror region and emitted to the predetermined region.

7. The endoscope according to claim 1, wherein the prism comprising a cuboid portion and a quadrangular-prism shaped portion, the quadrangular-prism shaped portion having an end surface obliquely formed at a predetermined angle;

the mirror region is disposed on the end surface;

the first light flux passes through the cuboid portion and the quadrangular-prism shaped portion and being emitted to the predetermined region;

the second light flux is incident on the quadrangular-prism shaped portion, incident on the end surface, reflected by the mirror region and emitted to the predetermined region.

8. The endoscope according to claim 1, wherein the first decentered lens is configured to cause the first light flux emitted from the prism to be parallel to the optical axis of the imaging lens, and the second decentered lens is configured to cause the second light flux emitted from the prism to be parallel to the optical axis of the imaging lens.

9. The endoscope according to claim 1, wherein the first decentered lens and the second decentered lens each has a structure obtained by cutting at least a part of a plane-convex lens.

10. An adaptor for attachment to an insertion portion of an endoscope, the endoscope having an imaging sensor and an imaging lens configured to form images on the imaging sensor, the adaptor comprising:

a first concave lens, a first light flux from a first region of a subject being incident on the first concave lens;

a second concave lens, a second light flux from a second region of the subject being incident on the second concave lens, the second light flux being in a direction orthogonal to the first light flux, the second region being different from the first region;

a prism comprising a mirror region, the first light flux and the second light flux each being incident on the prism, the first light flux and the second light flux passing through the prism at an intersecting portion of the prism, the second light flux being reflected by the mirror region after passing through the intersecting portion, the first light flux and the second light flux being emitted from the prism to a predetermined region; and a light-shield disposed at the predetermined region, the light-shield comprising two holes through which the first light flux and the second light flux pass through, respectively, the light-shield being configured to selectively shield one of the two holes;

wherein the light shield is disposed between the prism and a distal end of the insertion portion of the endoscope when the adaptor is attached to the insertion portion;

the first concave lens is disposed such that the first light flux from the first concave lens being incident in a direction substantially parallel to an optical axis of the imaging lens and directed toward a center of the image sensor, the first light flux being disposed only on a first side of an optical axis of the imaging lens; and the second concave lens is disposed so that the second light flux from the second concave lens being incident in a direction substantially orthogonal to the optical axis of the imaging lens and directed toward a center of the image sensor, the second light flux being disposed only on a second side of the optical axis of the imaging lens, the first side and the second side are offset in a direction perpendicular to the optical axis of the imaging lens with the second side being opposite to the first side relative to the optical axis;

the adaptor further comprising:

a first decentered lens disposed on the first side of the optical axis, the first decentered lens being configured to deflect the first light flux such that a part of the first light flux emitted from the prism and passing through a center of one of the two holes reaches a center of an image formed on the image sensor, the part of the first light flux being inclined with respect to the optical axis of the imaging lens; and a second decentered lens disposed on the second side of the optical axis, the second decentered lens being configured to deflect the second light flux such that a part of the second light flux emitted from the prism and passing through a center of an other of the two holes reaches the center of the image formed on the image sensor, the part of the second light flux being inclined with respect to the optical axis of the imaging lens;

wherein the first light flux passes through the first decentered lens, the one of the two holes of the light shield and then is incident on the imaging lens, the second light flux passes through the second decentered lens, the other of the two holes of the light shield and then is incident on the imaging lens.

11. The adapter according to claim 10, wherein the prism is disposed such that the first light flux is emitted toward a region of the prism other than the mirror region; and the second concave lens is disposed such that the second light flux is emitted toward the mirror region.

12. The endoscope according to claim 11, wherein the mirror region is disposed in a region of the prism such that the first light flux is not incident on the mirror region.

13. The adapter according to claim 10, wherein the prism comprising a cuboid portion and a quadrangular-prism shaped portion, the quadrangular-prism shaped portion having an end surface obliquely formed at a predetermined angle;

the mirror region is disposed on the end surface;

the first light flux passes through the cuboid portion and being emitted to the predetermined region;

the second light flux passes through the cuboid portion, is subsequently incident on the end surface, reflected by the mirror region and emitted to the predetermined region.

14. The adapter according to claim 10, wherein the prism comprising a cuboid portion and a quadrangular-prism shaped portion, the quadrangular-prism shaped portion having an end surface obliquely formed at a predetermined angle;

the mirror region is disposed on the end surface;

the first light flux passes through the cuboid portion and the quadrangular-prism shaped portion and being emitted to the predetermined region;

the second light flux is incident on the quadrangular-prism shaped portion, incident on the end surface, reflected by the mirror region and emitted to the predetermined region.

* * * * *